United States Patent [19]

Mesek

[11] 4,024,867
[45] May 24, 1977

[54] DISPOSABLE DIAPER WITH PERMANENTLY ATTACHED ADHESIVE BELT FASTENING MEANS

[75] Inventor: Frederick K. Mesek, Downers Grove, Ill.

[73] Assignee: Johnson & Johnson, New Brunswick, N.J.

[22] Filed: Feb. 18, 1976

[21] Appl. No.: 658,986

Related U.S. Application Data

[63] Continuation of Ser. No. 561,018, March 21, 1975, abandoned.

[52] U.S. Cl. .................................. 128/287; 128/284
[51] Int. Cl.² .......................................... A61F 13/16
[58] Field of Search .......... 128/284, 287; 24/73 VA

[56] References Cited

UNITED STATES PATENTS

| 2,834,347 | 5/1958 | Connally | 128/284 |
| 3,610,244 | 10/1971 | Jones, Sr. | 128/287 |
| 3,642,001 | 2/1972 | Sabee | 128/287 |
| 3,750,669 | 8/1973 | De Luca | 128/287 |
| 3,794,038 | 2/1974 | Buell | 128/287 |
| 3,853,129 | 12/1974 | Kozak | 128/287 |
| 3,862,634 | 1/1975 | Small | 128/284 |
| 3,869,761 | 3/1975 | Schaar | 24/73 VA |
| 3,874,386 | 4/1975 | Kozak | 128/287 |
| 3,875,621 | 4/1975 | Karami | 128/287 X |
| 3,890,973 | 6/1975 | Davis | 128/284 |

Primary Examiner—Aldrich F. Medbery

[57] ABSTRACT

A disposable diaper is provided with an adhesive closure means in which an elongated flexible strip extends transversely across the diaper along a marginal portion thereof. The strip has a mid-portion which is permanently attached to the diaper, and a pair of end portions. Each end portion has an inward section which has a release coating on the inside surface, and a free end section which has an adhesive coating on the inside surface. The free end section is adapted for folding over upon the inward section and releasably adhering thereto. In one embodiment, the inward section is positioned along a side margin of the diaper so that each free end section, when ready for use, extends beyond an adjacent edge of the diaper. In another embodiment, the entire length of each end portion extends beyond a side edge of the diaper. In both of these embodiments, an elongated separator means may be attached to the free end section to provide a gripper for peeling the free end away from the inward section for fastening the diaper about a baby.

9 Claims, 14 Drawing Figures

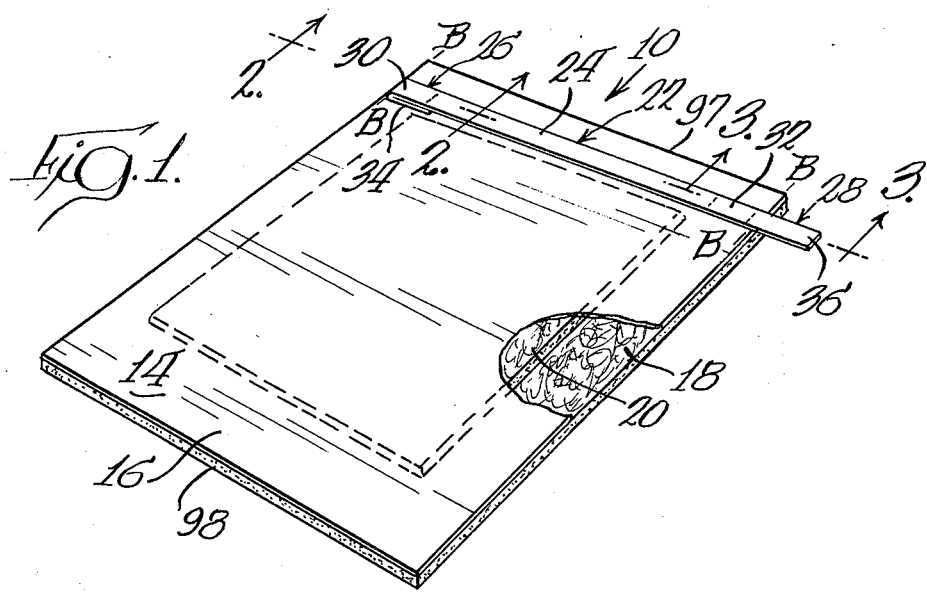
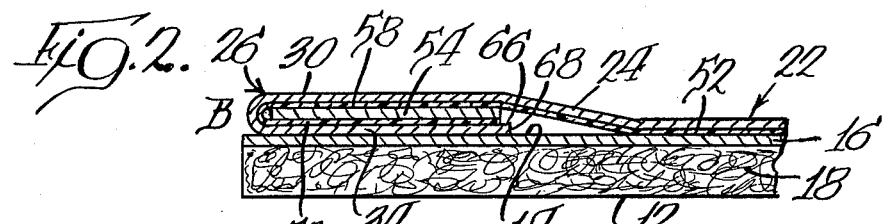
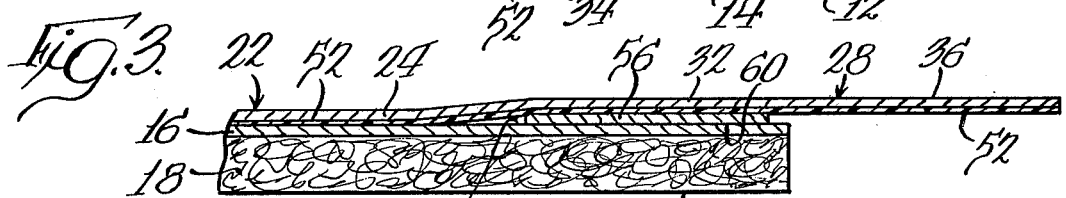
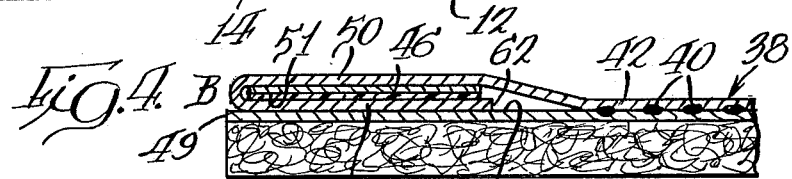
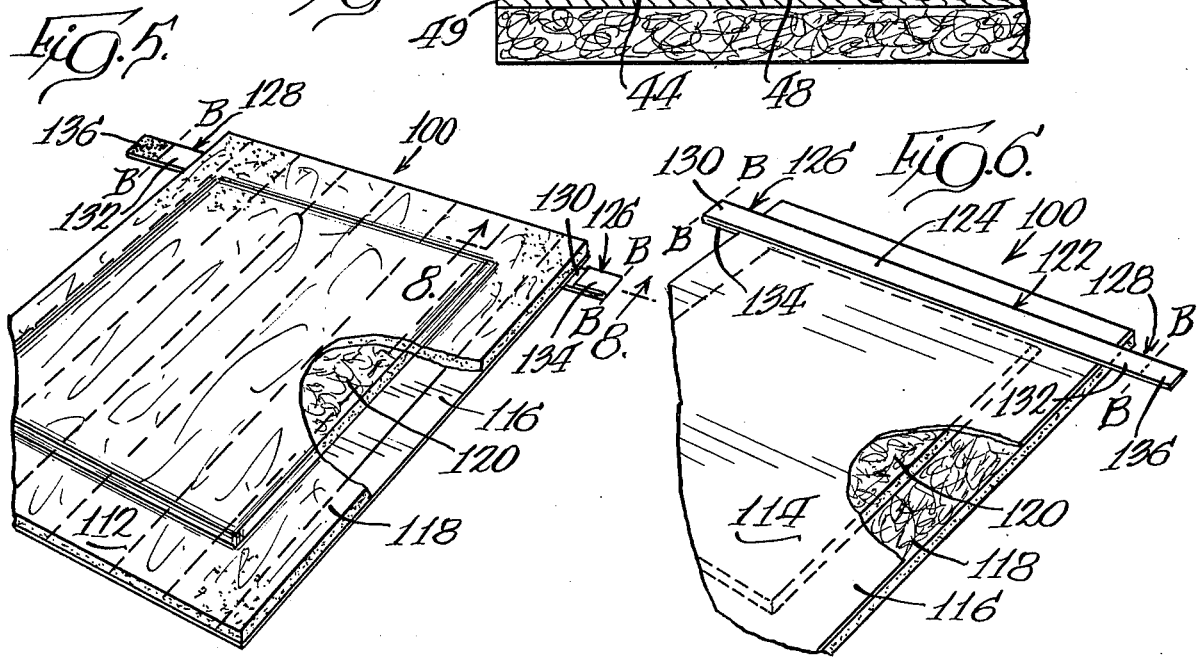
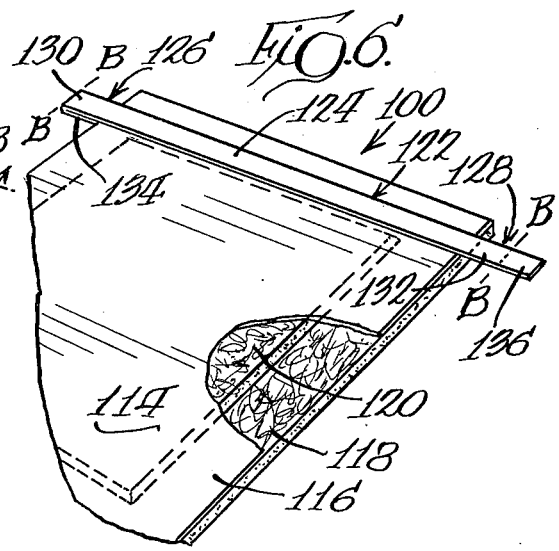

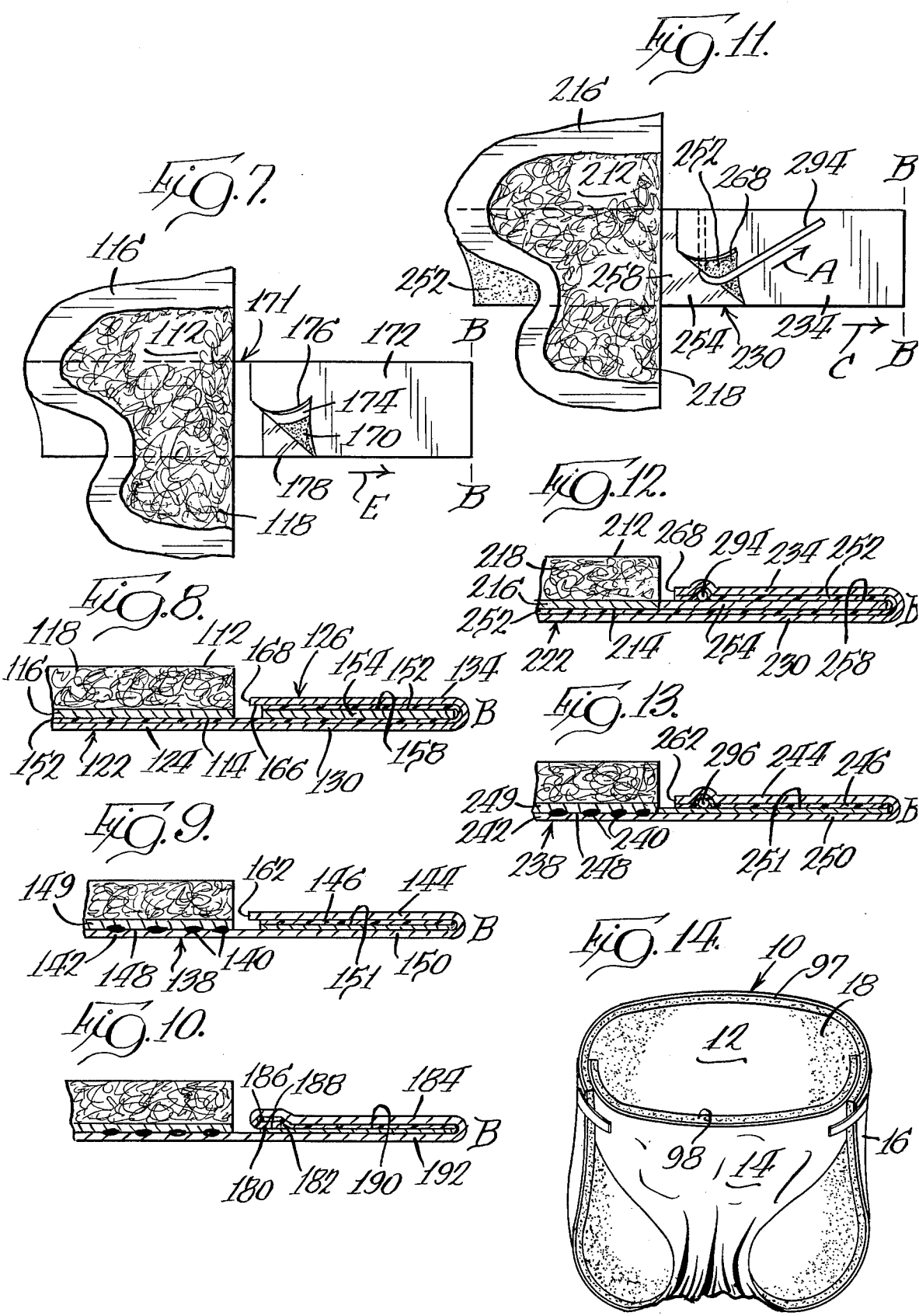

DISPOSABLE DIAPER WITH PERMANENTLY ATTACHED ADHESIVE BELT FASTENING MEANS

This is a continuation of application Ser. No. 561,018 filed Mar. 21, 1975 and now abandoned.

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

One of the most convenient adhesive systems that has been developed to date is the system, shown in the above-cited patents, in which adhesive tabs are adhered to the backing sheet extending outwardly from opposite sides of the diaper at one end thereof, and in which the exposed areas of the adhesive strips are provided with readily separable cover strips which protect the exposed areas until ready for use. However, disposable diapers using an adhesive closure system of this general type have the disadvantage that the consumer has to dispose of the cover strips when they are separated from the adhesive tabs. This is an inconvenience to the consumer who is placing the diaper on a baby at about the same time.

An illustrative prior art adhesive system having cover strips permanently attached to the diaper is disclosed in U.S. Pat. No. 3,646,937 to Gellert. The Gellert arrangement has the disadvantage of having a release film permanently anchored to the inside surface of the diaper, where it can possibly come into contact with a baby's tender skin. Additional disadvantages are the complexities and expense which are added to the manufacturing process by requiring each adhesive closure to be manipulated on the from side, around the edge, and on to the back side of the diaper, instead of handling the adhesive closure on one side only.

Another prior art patent, U.S. Pat. No. 3,049,124 to Thompson, avoids the use of cover strips by utilizing tie strings which extend transversely across the entire width of the diaper. In the Thompson arrangment, however, the tie strings are part of a rubber panty into which disposable diaper is positioned, and the tie strings are positioned on the inside surface of the panty where it will contact a baby's skin. Additional disadvantages include the need for at least two strings extending transversely across the diaper because of the requirement of tying one string to an opposite side.

In U.S. Pat. No. 3,847,702 to Jones, a pair of non-extensible reinforcing waist bands are secured to a relatively thin fluid impermeable backing sheet of a diaper. The reinforcing waistbands extend transversely across the backing sheet at each end of the diaper and are intended for adhesive securement to each other. Both ends of at least one of the bands have adhesive coated areas which are adhesively bonded to the other band at the opposite end of the diaper. Two such bands are required because the fluid impermeable backing sheet is only 0.0003–0.0005 inch thick and would cold stretch on tensile loading if the adhesive areas at the ends of one of the waistbands were bonded directly to the backing sheet.

SUMMARY OF THE INVENTION

In this invention, an adhesive tab fastener for a diaper comprises an elongated flexible strip, which forms a belt extending transversely across the diaper along a marginal portion thereof. A mid-portion of the strip is permanently attached to the diaper, and the end portions of the strip have an inward section which has a release coating on the inside surface, and a free end section which has an adhesive coating on the inside surface. Each free end section is folded over upon the corresponding inward section which has the release coating so that the free end section can be made available when needed.

In a first embodiment, the inward section is positioned along a marginal side portion within the boundaries of the diaper so that each free end section, when ready for use, extends beyond the side edge of the diaper.

In a second embodiment, the entire length of each end portion of the strip extends beyond an adjacent side edge of the diaper.

In both of the above embodiments, the inward section of the end portion of the strip is provided with a release surface, i.e., with a release coating on the inside surface or alternatively with an adhesive coating on the inside surface to which a release strip is adhered. One face of the release strip is attached to the adhesive coating and the opposite outer face of the release strip is coated with a release coating. Where a release strip is employed, both the free end section and inward section of the end portion have an adhesive coating on the respective inside surfaces thereof. The adhesive coating may also extend along the entire length of the elongated flexible strip, in which case the inward section of each end portion has a release strip with a release coated surface, and the mid-portion of the elongated flexible strip is adhered to the diaper by means of the adhesive coating.

Both the first and second embodiments described above may also employ an elongated separator means which may be interposed between the inward section and free end section when the free end section is folded over the inward section. The separator means is adhered to the free end section and extends beyond the perimetric limits of the free end section to provide a gripper for peeling each free end section away from the corresponding inward section for fastening the diaper about a baby. A short length of string may be used as the separator means.

A gripping means may also be provided by having the adhesive coating on each free end section extend across the entire face of the free end section except for a segment at the distal end of the free end portion. Alternatively, a segment of the free end section at the distal end thereof may be folded inwardly and adhered to an adjacent segment of the free end section so as to provide a gripping means.

By utilizing a continuous strip of material that extends across the entire transverse dimension of a diaper along a marginal portion thereof the area of attachment for a tab to the diaper is increased. In addition, since the continuous strip of material provides a continuous bond around the back portion of the diaper when the diaper is worn by an infant, a likelihood that the adhesive tabs may be pulled away from the diaper backing sheet as the infant moves about is obviated. Also, with the adhesive tab fastener means at each end of the strip minimally protruding beyond a marginal side edge of the diaper while the adhesive surface of each free end section is protected by attachment to a release surface, the present invention obviates problems encountered with prior art adhesive tabs wherein the adhesive tabs interfere with the folding and packing machinery used in the manufacture of the diapers. The present invention provides convenient and inexpensive adhesive tab fasteners which are permanently secured to a diaper.

BRIEF DESCRIPTION OF THE DRAWINGS

FIG. 1 is a perspective view, partly broken away to show interior detail, of the back side of an open, unfolded diaper in accordance with one embodiment of this invention;

FIG. 2 is a fragmentary cross-sectional view of the diaper of FIG. 1 taken along plane 2—2 and shown on an enlarged scale;

FIG. 3 is a fragmentary cross-sectional view of the diaper of FIG. 1 taken along plane 3—3 and shown on an enlarged scale;

FIG. 4 is a fragmentary cross-sectional view similar to FIG. 2 illustrating an alternate embodiment of the invention;

FIG. 5 is a perspective view, partly broken away to show interior detail, of an open, unfolded diaper in accordance with another embodiment of this invention;

FIG. 6 is a perspective view, partly broken away, of the back side of the open, unfolded diaper of FIG. 5;

FIG. 7 is a partial top plan view illustrating the tab partially separated in preparation for use;

FIG. 8 is a fragmentary cross-sectional view of the diaper of FIG. 5 taken along plane 8—8 and shown on an enlarged scale;

FIG. 9 is a fragmentary cross-sectional view similar to FIG. 8, illustrating an alternate embodiment of the invention;

FIG. 10 is a fragmentary cross-sectional view, similar to FIG. 9, illustrating an alternate embodiment of the invention;

FIG. 11 is a partial top plan view similar to FIG. 7, illustrating an alternate embodiment of the invention;

FIG. 12 is a fragmentary cross-sectional view of the tab of FIG. 11;

FIG. 13 is a fragmentary cross-sectional view similar to FIG. 12, illustrating an alternate embodiment of the invention; and FIG. 14 is a perspective view on reduced scale of the diaper of FIGS. 1, and 2 and 3 shown in the configuration assumed after the diaper is placed on the infant.

DESCRIPTION OF THE PREFERRED EMBODIMENTS

In the following description, two digit numerals are used to refer to the embodiments illustrated in FIGS. 1–4 and 14, three digit numerals 100 and 199 are used to refer to the embodiments illustrated in FIGS. 5–10, and three digit numerals 200 to 299 are used to refer to the embodiments illustrated in FIGS. 11–13. Except where otherwise indicated, the same last two digits in each numeral designate similar elements in the various embodiments.

Disposable diaper 10, illustrated in FIGS. 1 and 14, is of substantially quadrilateral configuration and has a porous, moisture-permeable facing layer 18, usually of fibrous material, defining a diaper inside surface 12 which is directed toward an infant when worn by that infant, and a moisture-impervious backing sheet 16 which overlies facing layer 18, is substantially coextensive therewith, and defines diaper outside surface 14.

Diaper 10 also preferably includes highly moisture-absorbent fibrous pad or batt 20, which is also rectangular in shape, but smaller than the facing and backing layers and is centrally disposed therebetween. Batt 20 may be formed in accordance with the teachings set forth in commonly assigned U.S. Pat. No. 3,612,055 to Mesek et al. Alternatively, a highly moisture-absorbent layer can be provided substantially coextensive with the backing sheet 16 if desired.

Moisture-impervious sheet 16 may be formed of polyethylene having a thickness of approximately 0.001. The sheet may be smooth or may be embossed to improve its drape and feel. Other suitable flexible moisture-impervious sheets may be used such as, for example, polyethylene terephthalate sheets having a thickness of about 0.0005, and the like.

The present invention contemplates that several different types of facing layers may be used for the diaper. For example, facing layer 18 may be made up of a moisture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing layers suitable for use in this invention can have fabric weights in the range of 1 to 5 oz/yd.$^2$ and densities less than 0.15 gm./cc., generally in the range between 0.05 and 0.10 gm/cc. The dry strength of the facing layer, for a fabric having a weight of about 1.5 oz./yd.$^2$, is at least 0.15 lbs./in. of width in the machine direction and at least 0.10 lbs./in. of width in the cross direction. These fabrics have unusually good elongation, loft, softness, and drape characteristics in comparison to prior products incorporating any substantial amount of short fibers.

Facing layer 18 may be also an apertured nonwoven fabric formed, for example, in accordance with the teachings in commonly assigned U.S. Pat. Nos. 2,862,251; 3,081,514; and 3,081,515. Briefly, such fabrics are foraminous structure wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well understood by those skilled in the art. A suitable binder may be utilized to help retain the fibers in their rearranged locations, as is also well understood by those skilled in the art. The fabric can be made of naturally occurring fibers, synthetic fibers or blends thereof. Typical facing layers made of a polyester material may have a weight of ¾ oz./yd.$^2$.

It should also be understood that the facing layer may be formed of a nonapertured material, such as a nonwoven isotropic web, sponge, or the like. In all of the aforementioned facings, the materials should be relatively hydrophobic so as to retard wicking within the facing layer.

Referring to FIGS. 1, 2 and 3, diaper 10 has an adhesive tab fastener which comprises an elongated flexible strip 22 which forms a belt extending transversely across the diaper along a marginal portion thereof. Mid-portion 24 of strip 22 is permanently attached to the diaper outside surface 14 and end portions 26 and 28 of strip 22 each have respective inward sections 30 and 32 and respective free end sections 34 and 36. Strip 22 is preferably inwardly spaced from distal end 97 of diaper 10.

The belt-like adhesive tab fastener of the present invention may be positioned between the diaper backing sheet and facing sheet, rather than on the outside surface of the diaper, as long as the strip is secured to the backing sheet.

Elongated flexible strip 22 may be a polyethylene ribbon or may be formed of other flexible materials such as polyethylene-nylon laminates, polyethylene terephthalate, and the like.

This invention contemplates various configurations for elongated flexible strip 22 and various embodiments by which inward sections 30 and 32 of strip 22 are provided with a release coated surface to which free end sections 34 and 36 are releasably adhered. In one embodiment, FIG. 1—3, inward sections 30 and 32 are positioned along opposite side margins of diaper 10 so that the corresponding free end sections 34 and 36, when ready for use, extend beyond corresponding adjacent side edges of the diaper, but are retained within the peripheral limits of the diaper before the diaper has been prepared for use.

In another embodiment, illustrated in FIGS. 5 and 6, diaper 100 is the same in all respects to the diaper 10 in FIS. 1 and 14 with the exception of elongated flexible strip 122. Thus, diaper 100 has inside surface 112 directed toward an infant and outside surface 114 directed away from an infant. Diaper 100 also has backing sheet 116, absorbent pad 120 and facing sheet 118. Strip 122 has mid-portion 124 and end portions 126 and 128. Each end portion has respective inward sections 130 and 132 adjacent to mid-portion 124 and respective free end sections 134 and 136. Strip 122 in FIGS. 5 and 6 differs from strip 22 in FIGS. 1 and 14 in that mid-portion 124 extends across the entire transverse dimension of the diaper so that the entire length of each end portion 126 and 128 of the strip extends beyond an adjacent side edge of the diaper.

As stated above, this invention also contemplates various embodiments by which the inward section of the tab is provided with a release coated surface to which the corresponding free end section of the strip i releasably adhered. As depicted in FIGS. 4 and 9, strip 38, 138 is provided with pressure sensitive adhesive coating 40, 140 on mid-portion 42, 142 which is permanently attached to the diaper, and with pressure sensitive adhesive coating 46, 146 on each free end section 44, 144. Strip 38, 138 can thus be adhesively attached to the backing sheet 49, 149. The adhesive on the mid-portion and end sections may be continuous or may be in spots. The adhesive is applied to the face of the strip which is juxtaposed to outside surface 48, 148 of the diaper and in contact therewith. Inward section 50, 150 is provided with a release coating such as a silicone coating, or the like, which presents a release surface 51, 151 between the adhesively coated surface 40, 140 on the mid-portion and the adhesively coated surface 46, 146 on the end section.

Referring to FIGS. 2, 3 and 8, the entire length of strip 22, 122 may be provided with a pressure sensitive adhesive coating 52, 152 on the face of the strip 22, 122 which is juxtaposed to outer surface 14, 114 of the diaper and in contact therewith. The tacky surface of each inward section is covered with release strip 54 and 56, 154 having one face permanently adhered to the adhesive coating 52, 152 and having an opposite face coated with a release coating 58 and 60, 158 and facing in the same direction as the adhesive coating 52, 152. The adhesive coating may be continuous (FIGS. 2, 3, 8 and 12) or in spots (FIGS. 9, 13). Mid-portion 24, 124 of the strip can thus be adhesively attached to diaper outside surface 14, 114.

Regardless of whether a release strip is employed, the adhesive coatings on free end sections 34 and 36, 134 are contiguous to the release coating on inward sections 30 and 32, 130 and each end portion 26 and 28, 126 is folded over upon itself about line B—B such that substantially the entire tacky surface of free end sections 34 and 36, 134 is releasably attached to the corresponding inward section 30 and 32, 130 of strip 22, 122.

A gripping means may also be provided for peeling each free end section away from corresponding inward section for fastening the diaper about a baby. As is shown in FIGS. 4 and 9, free end section 44, 144 adapted to be folded over may be slightly shorter than the corresponding inward section 50, 150 of the tab fastener means. The user can separate the free end section from the inward section by sliding a fingernail under adhesive-coated surface 46, 146 adjacent distal end 62, 162 of each free end section 44, 144. A segment of the free end portion adjacent distal end 62, 162 can then be gripped.

Alternatively, FIGS. 2 and 8 illustrate a construction wherein free end section 34, 134 adapted to be folded over is slightly longer than the corresponding inward section 30, 130 of the tab fastener means, such that a segment 66, 166 of the free end section adjacent distal end 68, 168 is not covered by release coated surfaces 58, 158 on release strip 54, 154 but rather projects beyond release coated surface 58, 158. Due to the thickness of the release strip 54, 154, a space exists between segment 66, 166 adjacent distal end 68, 168 of the free end section 34, 134 which provides a lift tab that readily enables the user to grip the free end section and peel the free end section from the corresponding release surface when preparing to fasten the diaper about a baby.

FIG. 7 illustrates a structure that further facilitates grasping of the free end section for peeling it away from the corresponding inward section. Strip 171 may be provided with an adhesive coating 170 which extends across the entire free end section 172 except for a segment 174 at the distal end 176 of the free end section 172. Segment 174 of free end section 172 thus provides a lift tab to be gripped when peeling the free end section away from the corresponding inward section 178 for fastening the diaper about a baby.

As illustrated in FIG. 10, a gripping means can also be provided by folding inwardly a narrow segment 180 at the distal end 182 of free end section 184 and adhering segment 180 to an adjacent portion of free end section 184. One face 186 of segment 180 is adhered to free end section 184, and the opposite face 188 is juxtaposed to the release coated surface 190 of inward section 192, thereby providing a folded over segment which can readily be grasped by a user.

Referring now to FIGS. 11–13, a gripping means may also be provided by attaching an elongated separator means 294, 296 to the free end section 234, 244. The elongated separator means may be a short length of string. Materials such as thread, nylon, or other plastic monofilaments are suitable for use as the separator means.

As illustrated in FIGS. 11 and 12, the entire length of strip 222 may have adhesive coating 252 on the face of the strip which is juxtaposed and in contact with the outer surface of the diaper in which case inward section 230 is covered with a release strip 254 having a release coated face 258. Alternatively, as shown in FIG. 13, strip 238 can have an adhesive coating 240 on one face of midportion 242 and an adhesive coating 246 on the same face of free end section 244, in which case inward section 250 has a release coating 251 on the face contiguous to the tacky face of mid-portion 242 free end section 244. Adhesive coatings 240 and 246 may be contiuous or in spots.

Separator string 294, 296 is interposed between free end section, 234, 244 and inward section 230, 250 when end portion 222, 238 is in the folded configuration and is held on the free end section by adhesive coating 252. Separator string 294, 296 is positioned transversely on tacky surface 252, 246 of free end section 234, 244 near distal end 268, 262 usually about ⅛ inch to about ¼ inch from distal end 268, 262 of free end section 234, 244 and extends beyond the perimetric limits of the free end section, protruding beyond free end section 234, 244 about ¼ to about 1 width thereof. For example, when free end sections 234, 244 is about one inch wide, string 294, 296 protrudes about ¼ inch to about 1 inch beyond the perimeter of free end section 234, 244 so that the protruding portion of string 294, 296 can be grasped by the user to peel the free end section 234, 244 away from the inward section 230, 250 for fastening the diaper about a baby. String 294, 296 remains permanently adhered to the free end section by adhesive coating 252, 246 or may be otherwise affixed to free end sections 234.

FIGS. 7 and 11 illustrate the use of a gripping means to separate the folded over free end section from the corresponding inward section to which it is releasably adhered. As shown in FIG. 11, separation is effected by grasping the free end section 234 near distal end 268, or grasping the protruding portion of string 294 between one forefinger and thumb, and peeling free end section 234 away from the corresponding inward section 230 by pulling in the direction indicated by arrow A, thereby lifting a portion of the distal end 268 of the folded over free end section 234. This enables the user to grasp free end section 234 near distal end 268 and pull in the direction indicated by arrow C. Alternatively, the embodiments illustrated in FIGS. 1 – 10 and 14 can be prepared for use as illustrated in FIG. 7 by sliding a fingernail under a segment at the distal end 176 of the free end section 172, lifting the free end section, and then pulling in the direction indicated by arrow E, or by grasping a segment of the distal end 176 of the free end section 172 between one forefinger and thumb, lifting the free end section, and then pulling in the direction of arrow E.

After the free end of each tab is totally separated from the corresponding inward section and the diaper is applied to the infant, all components of the adhesive closure means of this invention remain permanently attached to the diaper, thereby obviating the need for the user to dispose of a release strip or any other component of the closure means. Additionally, after the free end section of each tab is totally separated from the corresponding inward section and the diaper is applied to the infant, the exposed release coated surface of the inward section faces the outer surface of the diaper, where it will not come in contact with baby's tender skin. Another feature is that each adhesive tab can be readied for application of the diaper to the infant by using only one hand, thus leaving the user's other hand free for other purposes. A further advantage of the embodiment of this invention illustrated in FIGS. 4, 9 and 13 is the elimination of the need for any release strip. This is accomplished by having inward section 50, 150, 250 of the strip 38, 138, 238 provided with release coated surface 51, 151, 251 to which tacky surface 46, 146, 246 of free end section 44, 144, 244 of strip 38, 138, 238 is releasably adhered.

Suitable pressure-sensitive adhesives for the present purposes are known in the art and possess good tack, good cohesive strengh, good moisture resistance and good resistance to aging. Illustrative of such adhesive compositions are mixtures of natural or synthetic rubber with zinc oxide and various resins, natural or synthetic rubber or resin latices, tacky acrylic polymers or copolymers, and the like.

As illustrated in FIGS. 1 and 14, diaper 10 is applied to the infant by positioning the ends 97 and 98 of the diaper around the waist of the infant with the intermediate portion of the diaper disposed in the infant's crotch. Free end sections 26 and 28 of strip 22 are separated from the respective inward sections 30 and 32, and diaper ends 97 and 98 are pulled into tight fitting engagement with the infant's waist. The exposed portion of tacky surface on each free end section is then pressed against the adjacent portions of plastic backing sheet 16 on outside surface 14 of diaper 10. The final form assumed by diaper 10 in shown in perspective on a reduced scale in FIG. 14, and diaper 10 is held in this position by the adhesive closure system of the present invention.

The foregoing description and the drawings are illustrative but are not to be taken as limiting. Still other variations and modifications are possible without departing from the spirit and scope of this invention.

I claim:

1. A disposable diaper having an absorbent layer defining a diaper inside surface which is directed toward an infant when worn by that infant, a moisture-impervious backing sheet overlying said absorbent layer and defining a diaper outside surface, and an adhesive tab fastener means which comprises an elongated flexible strip extending transversely across said diaper along a marginal portion of said backing sheet, having a mid-portion thereof permanently attached to said backing sheet and a pair of end portions, each end portion having an inward section, unattached to and within the perimeter of said backing sheet and a free end section; a release coating on said inward section and facing in the same direction as said diaper inside surface; an adhesive coating on each said free end section and facing in the same direction as said release coating when the diaper is ready for use; each said free end section being adapted for folding over upon said inward section and releasably adhering thereto.

2. The diaper as set forth in claim 1, wherein said elongated flexible strip is adhesively attached to said backing sheet.

3. The diaper as set forth in claim 1, wherein said adhesive coating extends along one surface of each said end portion along the entire length thereof, and wherein said inward section comprises a release strip having one face permanently adhered to said adhesive coating and an opposite face coated with a release coating.

4. The diaper as set forth in claim 1, wherein said adhesive coating extends along one surface of said elongated flexible strip along the entire length thereof, wherein the mid-portion of said elongated flexible strip is attached to the diaper outside surface and said inward section of each said end portion comprises a release strip having one face permanently adhered to said adhesive coating and an opposite face coated with a release coating.

5. The diaper as set forth in claim 1, wherein each said free end section adapted to be folded over is slightly longer than the corresponding inward section of the tab fastener means.

6. The diaper as set forth in claim 1, wherein said elongated flexible strip has each said inward section positioned along a side margin of the diaper so that each free end section, when ready for use, extends beyond an adjacent side edge of said diaper.

7. The diaper as set forth in claim 1, wherein said elongated flexible strip is a polyethylene ribbon.

8. The diaper as set forth in claim 1, wherein said adhesive coating on each said free end section extends across the entire free end section except for a segment at the distal end of the free end section which segment provides a lift tab to be gripped when peeling said free end section away from said inward section for fastening said diaper about a baby.

9. The diaper as set forth in claim 1 wherein said elongated flexible strip has each said inward section positioned along a side margin of the diaper and within the peripheral limits of the diaper and wherein each said free end section is folded over the adjacent inward section and is releasably adhered thereto.

* * * * *